United States Patent

Bauer et al.

[11] Patent Number: 5,932,747
[45] Date of Patent: Aug. 3, 1999

[54] METHOD FOR PREPARING 1,3-DIOXANE COMPOUNDS

[75] Inventors: Frank Bauer, Köln; Manfred Neumann, Marl, both of Germany

[73] Assignee: Huels Aktiengesellschaft, Marl, Germany

[21] Appl. No.: 09/044,995

[22] Filed: Mar. 20, 1998

[30] Foreign Application Priority Data

Mar. 21, 1997 [DE] Germany ............... 197 11 758

[51] Int. Cl.$^6$ ............................................. C07D 319/06
[52] U.S. Cl. ........................... 549/369; 549/372; 549/376
[58] Field of Search ................... 549/372, 376, 549/369

[56] References Cited

U.S. PATENT DOCUMENTS

| | | | |
|---|---|---|---|
| 3,586,698 | 6/1971 | Ishii et al. | 549/376 |
| 5,144,046 | 9/1992 | Mathur | 549/376 |

FOREIGN PATENT DOCUMENTS

| | | |
|---|---|---|
| 0 220 034 | 4/1987 | European Pat. Off. . |
| 0 268 460 | 5/1988 | European Pat. Off. . |
| 40 40 685 | 6/1991 | Germany . |

OTHER PUBLICATIONS

S. Mager, et al., Studia Universitatis Babes–Bolyai–Chemia, vol. 24, No. 1, pp. 32–38, 1979, "$^1$H–NMR Spectra and Stereochemistry of Some 2,5–Substituted 1,3–Dioxanes".

Ernest L. Eliel, et al., Journal of the American Chemical Society, vol. 94, No. 1, pp. 171–176, Jan. 12, 1972, "Conformational Analysis. XXIV. Effect of Dipolar and Eclipsing Forces on Intramolecular Hydrogen Bonding in 3–Hydroxymethyltetrahydropyran and 5–Hydroxymethyl–1,3–Dioxane".

Kenneth N. Welch, Journal of the Chemical Society, pp. 257–261, 1930, "The Reactions of Malonic Esters with Formaldehyde".

Primary Examiner—John Kight
Assistant Examiner—Raymond Covington
Attorney, Agent, or Firm—Oblon, Spivak, McClelland, Maier & Neustadt, P.C.

[57] ABSTRACT

A method for preparing 1,3-dioxane compounds of the formula (I):

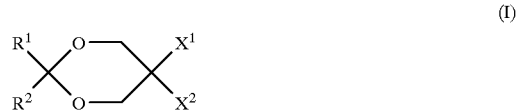

(I)

wherein $R^1$ and $R^2$, independently of one another, represent hydrogen or a hydrocarbon radical; and $X^1$ and $X^2$, independently of one another, represent an electronegative groups, which method entails reacting a bis(hydroxymethyl) compound of the formula (II):

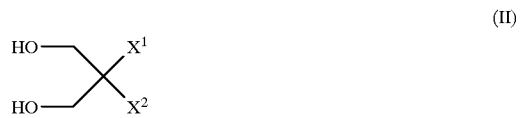

(II)

in which $X^1$ and $X^2$ each, independently of one another, are as defined above, with an orthocarboxylic acid ester of the formula $R^4$—$C(OR^5)_3$ (III), in which $R^4$ represents hydrogen or a hydrocarbon radical and $R^5$ represents a hydrocarbon radical, and with an aldehyde or ketone of the formula $R^1$—CO—$R^2$ (IV), in which R and R each, independently of one another, are as defined above.

18 Claims, No Drawings

METHOD FOR PREPARING 1,3-DIOXANE COMPOUNDS

BACKGROUND OF THE INVENTION

1. Field of the Invention

The present invention relates to a method for preparing 1,3-dioxane compounds.

2. Description of the Background 1,3-dioxane compounds of the formula (I):

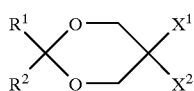

(I)

wherein $R^1$ and $R^2$ are each, independently of the other, hydrogen or hydrocarbon radical; and $X^1$ and $X^2$ are identical or different electronegative groups; are presently used as intermediates for the preparation of UV stabilizer or X-ray contrast media. See, for example, EP-A2 0 220 034.

1,3-Dioxane compounds of the general formula I are usually prepared from the corresponding bis(hydroxymethyl)compounds II by acid-catalyzed acetalization or ketalization in accordance with the reaction equation:

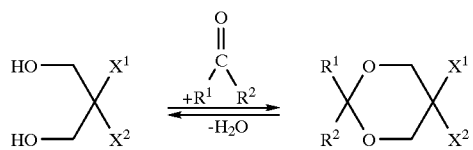

(see e.g. Mager, S.; Hopartean, I.; Horn, M.; Groso, I.; Stud. Univ., Babes-Bolyai, [Ser.] Chem. 1979, 24(1), 23-8). The shift of equilibrium in this case is effected by azeotropic distillation, using a suitable entrainer, such as toluene or cyclohexane.

Conducting this method on an industrial scale presents problems, however, which predominantly result from the thermal sensitivity of the bis(hydroxymethyl) compounds. For example, the industrially important diethyl bis(hydroxymethyl)malonate decomposes from temperatures of as little as 50° C. or higher, giving rise to numerous byproducts, inter alia formaldehyde (Welch, K. N.; J. Chem. Soc. London, 1930, 1). In the case of bis(hydroxymethyl) compounds containing cyano groups there is the further risk of toxic hydrogen cyanide being formed.

Thus, as expected, when industrially useful residence times are utilized, even if low-boiling entrainers such as toluene, cyclohexane or isopropyl acetate are used, product losses of up to 50% of the theoretical amount are observed, depending on the catalyst used.

On a laboratory scale it is possible to limit the bottom temperature to 50° C., and thus avoid thermal decomposition reactions, simply by applying a vacuum. In this case, for example, the reaction of diethyl bis(hydroxymethyl)malonate with an equimolar amount of cyclohexanone in toluene, catalyzed by sulfuric acid, affords an isolated yield of >85% of the theoretical yield. On an industrial scale, however, the condensation of the vapors entails very high investment and operating costs.

Thermal decomposition of the bis(hydroxymethyl) compounds under the reaction conditions of the acetalization or ketalization can also be avoided by the use of low-boiling entrainers (Eliel, E. L.; Banks, H. D.; J. Am. Chem. Soc. 94 (1972), 171). However, it has been found that low-boiling entrainers such as petroleum ether (30–60° C.), methyl t-butyl ether or methyl acetate shift the above-described equilibrium only very slowly and, moreover, in the case of sterically hindered ketones not all the way. The achievable space-time yields are, therefore, entirely inadequate for industrial implementations. Further arguments against implementing this procedure on an industrial scale include the high flammability of low-boiling petroleum ethers (flash point <20° C.) and the usually low solubilities of the highly polar bis(hydroxymethyl) compounds.

Thus, a need exists for a method which affords a rapid and complete conversion of the bis(hydroxymethyl)compounds into the compounds of the formula (I) under conditions in which product losses due to thermal decomposition of the starting materials are virtually precluded.

SUMMARY OF THE INVENTION

Accordingly, it is an object of the present invention to provide a method of forming compounds of the formula (I) under conditions in which product losses due to thermal decomposition of the starting materials are virtually precluded.

It is also an object of the present invention to provide a method of forming compounds of the formula (I) from bis(hydroxymethyl)compounds with rapid conversion.

The above objects and others are provided by a method for preparing 1,3-dioxane compounds of the formula (I):

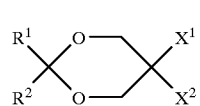

(I)

in which $R^1$ and $R^2$ are each, independently of one another, hydrogen or hydrocarbon radical; and $X^1$ and $X^2$ are each, independently of one another, the same or different electronegative groups; which process entails:

reacting a bis(hydroxymethyl) compound of the formula (II):

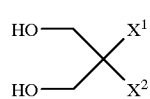

(II)

wherein $X^1$ and $X^2$ are as defined above, with an orthocarboxylic acid ester of the formula (III):

(III)

wherein $R^4$ is hydrogen or hydrocarbon radical; and $R^5$ is hydrocarbon radical; and with an aldehyde or ketone of the formula (IV):

(IV)

wherein $R^1$ and $R^2$ are each, independently of one another, are as defined above.

DETAILED DESCRIPTION OF THE PREFERRED EMBODIMENTS

The present invention provides a method for preparing 1,3-dioxane compounds of the formula (I):

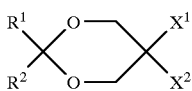
(I)

in which $R^1$ and $R^2$, independently of one another, represent hydrogen or a hydrocarbon radical, and $X^1$ and $X^2$ represent identical or different electronegative groups. Quite advantageously, bis(hydroxymethyl) compounds may be used to prepare compounds of the general formula I under conditions in which product losses due to thermal decomposition of the starting materials are virtually precluded.

It was found that this object is achieved in a simple manner and that 1,3-dioxane compounds of the formula (I):

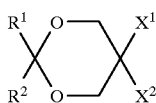
(I)

in which $R^1$ and $R^2$, independently of one another, represent hydrogen or a hydrocarbon radical, and $X^1$ and $X^2$, independently of one another, represent an electronegative group, are obtained advantageously if a bis(hydroxymethyl) compound of the formula (II):

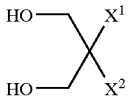
(II)

in which $X^1$ and $X^2$ each, independently of one another, as defined above, is reacted with an orthocarboxylic acid ester of the formula (III):

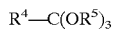
$R^4$—$C(OR^5)_3$ (III)

in which $R^4$ represents hydrogen or a hydrocarbon radical and $R^5$ represents a hydrocarbon radical, and with an aldehyde or ketone of the formula (IV):

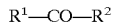
$R^1$—CO—$R^2$ (IV)

in which $R^1$ and $R^2$ each, independently of one another, are as defined above.

Under the very gentle conditions of the present method, the first reaction step occurring, most likely, entails a very rapid conversion of the bis(hydroxymethyl) compounds (II) into compounds of the formula (V):

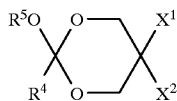
(V)

in which $R^4$, $R^5$, $X^1$ and $X^2$ are as defined above. Thus the sensitive bis(hydroxymethyl) compound (II) rapidly escapes conditions under which it tends to decompose. The compound (V), a cyclic orthocarboxylic acid ester, is stable under these conditions and reacts, in a second reaction step, with the aldehyde or ketone of the general formula (IV) to yield the 1,3-dioxane compound of the formula (I), a cyclic acetal or ketal.

In an advantageous embodiment of the present method according to the invention, the bis(hydroxymethyl) compound (II) is successively reacted with the orthocarboxylic acid ester (III) and the aldehyde or ketone (IV). In keeping with the abovementioned scenario entailing two individual steps, it is advantageous for the bis(hydroxymethyl) compound of the formula (II) first to be admixed with the orthocarboxylic acid ester of the formula (III) and then for the reaction mixture to be admixed with the aldehyde or ketone of the formula (IV). In principle, however, the order in which the reactants (III) and (IV) are added can be chosen at will. Thus, the two reactants can be introduced simultaneously or with a time overlap. Because of the very different reaction rates of the partial reactions mentioned, it is even possible to add the orthocarboxylic acid ester of the formula (III) after all the aldehyde or ketone of the formula (IV) has been added. Even then, yields and space-time yields are achieved which are surprisingly superior to those of the prior art. The following reaction schematics are noted:

For the reaction of diethyl bis(hydroxymethyl)malonate with triethyl orthoformate and acetone, the present method is reflected in the following reaction scheme:

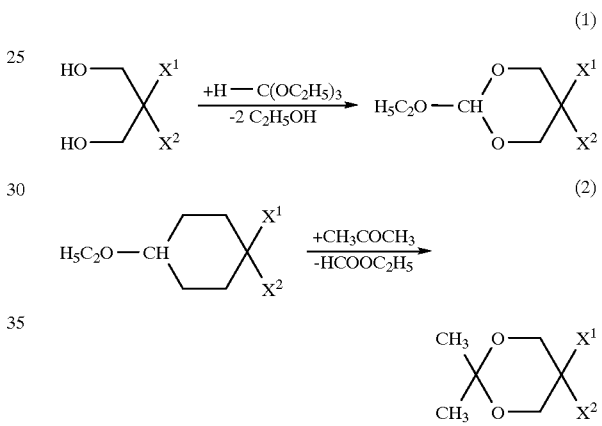

In the preferred 1,3-dioxane compounds of the formula (I), $R^1$ and $R^2$ each, independently of one another, represent hydrogen, alkyl, aralkyl, aryl or cycloalkyl, each having up to 12 carbon atoms, and may also jointly denote an alkylene radical having from 4 to 11 carbon atoms, and $X^1$ and $X^2$ each, independently of one another, represent COOR, $CONR_2$, CN, $NO_2$, C(OR)=NR or COR, wherein R is hydrogen, alkyl, aralkyl, aryl or cycloalkyl, each having up to 12 carbon atoms; with the proviso that (i) the substituents $X^1$ and $X^2$ cannot both simultaneously represent COOH, and (ii) if the two substituents $X^1$ and $X^2$ simultaneously represent COR, the two substituents R may also represent an alkylene radical having from 2 to 9 carbon atoms.

In the particularly preferred 1,3-dioxane compounds (I), $X^1$ and $X^2$ each independently represent CN or COOR', and R' is a $C_{1-4}$-alkyl radical.

In the preferred bis(hydroxymethyl) compounds of the formula (II), $X^1$ and $X^2$ each, independently of one another, are as defined for the preferred 1,3-dioxane compounds of the formula (I). Examples of the preferred bis (hydroxymethyl) compounds are dimethyl bis (hydroxymethyl)malonate, diethyl bis(hydroxymethyl) malonate, di-n-propyl bis(hydroxymethyl)malonate, diisobutyl bis(hydroxymethyl)malonate, dibenzyl bis (hydroxymethyl)malonate, di-2-ethylhexyl bis (hydroxymethyl)malonate, ethyl bis(hydroxymethyl)-N,N-dimethylcarbamidoacetate, bis(hydroxymethyl)-N,N,N',N'- tetramethylmalonanide, bis(hydroxymethyl)malononitrile, ethyl bis(hydroxymethyl)cyanoacetate, n-butyl bis-(hydroxymethyl)cyanoacetate, ethyl bis(hydroxymethyl) nitroacetate, 3,3-bis(hydroxymethyl)acetylacetone and 2,2-bis(hydroxymethyl)cyclododeca-1,3-dione. In the particularly preferred bis(hydroxymethyl) compounds (II), $X^1$ and $X^2$ are as defined for the particularly preferred 1,3-dioxane compounds, i.e. CN or COOR'.

Preferred orthocarboxylic acid esters of the formula (III) are the orthoformic acid esters ($R^4$=H) of alkanols having from 1 to 4 carbon atoms ($R^5$=$C_{1-4}$-alkyl). Examples of these are triethyl orthoformate, triisobutyl orthoformate and, particularly preferred, trimethyl orthoformate. If the substituents $X^1$ and/or $X^2$ in the bis(hydroxymethyl) compound of the formula (II) represent —COOR, and R differs from $R^4$ and/or $R^5$ in the formula (III), transesterification may take place. Remarkably this is not the case, so that the choice of the orthocarboxylic acid esters is not subject to any restrictions. The orthocarboxylic acid ester is advantageously used in at least a stoichiometric amount. If employed in excess it serves as a solvent at the same time. In some cases it may also be advisable to employ, in addition, an inert solvent, e.g. an alkanol, as will be explained below in more detail.

In the preferred aldehydes or ketones of the formula (IV), $R^1$ and $R^2$, independently of one another, are as defined for the preferred 1,3-dioxane compounds of the formula (I). Examples of the preferred aldehydes and ketones are formaldehyde, acetaldehyde, n-butyraldehyde and isobutyraldehyde, benzaldehyde, phenylacetaldehyde, acetone, methyl ethyl ketone, diisopropyl ketone, cyclohexanone and cyclododecanone. The aldehyde or ketone (IV) is expediently likewise employed in a stoichiometric amount or in excess, e.g. of up to 200%. Even greater excesses will reduce the space-time yield.

The present method can be implemented even below room temperature. Above 40° C. the reaction is usually complete within a few hours. Particular preference is therefore given, in batch mode, to a temperature in the range from about 0° C. to 80° C., in particular from about 20 to 50° C. In practice it proved advantageous to raise the temperature toward the end of the reaction, e.g. by about 10° C. to 30° C. The reaction temperature and the reaction time should be tailored to one another so as to ensure that decomposition reactions are virtually precluded. Advantageously the reaction temperature is chosen is such that low-boiling components formed during the reaction, such as alkanols and alkyl formates, will distill off from the reaction mixture. If the residence times are adequately shortened by suitable measures, in particular by the reaction being carried out in continuous mode, the method can alternatively be implemented at far higher temperatures such as about 200° C. and more, involving correspondingly short reaction times.

A suitable choice of reaction temperature and reaction time allows the decomposition of the bis(hydroxymethyl) compound of the formula (II) to be largely suppressed in the present method, even under industrial conditions. The yields of 1,3-dioxane compounds of the formula (I) are higher, accordingly, than the yields achieved by the azeotropic method. For example, the preparation of diethyl 2-isopropyl-1,3-dioxane-5,5-dicarboxylate according to the present method gave yields of up to 82% of the theoretical yield. This value is to be compared with a yield of 77% of the theoretical yield (Eliel et al., loc. cit.) which, to make things worse, was achieved by azeotropic distillation with petroleum ether (30 to 60° C.) as the entrainer and thus in a way which is not suitable for industrial applications. Higher-boiling entrainers resulted in even lower yields of the intended product (Eliel et al., loc. cit.).

The bis(hydroxymethyl) compounds of the formula (II) can be used in the pure form or alternatively as solutions in inert solvents, advantageously in alcohols such as ethanol. At any rate, the bis(hydroxymethyl) compound or its solution should be substantially anhydrous. If this is not the case, the water content can be taken into account by a corresponding increase in the amount of orthocarboxylic acid ester of the formula (III).

The present method is implemented particularly advantageously by preparing the bis(hydroxymethyl) compound of the formula II by reacting C-H-acidic compounds of the formula (IV):

(VI)

in which $X^1$ and $X^2$ are as defined above, with formaldehyde or a formaldehyde-releasing compound, if appropriate in an inert solvent, and without isolation being reacted in the reaction mixture. It is advantageous to use an orthocarboxylic acid ester of the formula (III) (or a mixture of such esters) as the solvent, expediently following the method of copending U.S. patent application (U.S. attorney docket no. 0689-0759-0). The orthocarboxylic acid ester (III) reactant serves in this precursor stage as a solvent, so that use of a further inert solvent may be partially or completely avoided. For the reaction according to the present invention the orthocarboxylic acid ester then acts as reactant (III). This "one-pot method" represents a simplification of the procedure according to the present invention, makes the equipment required less complicated and optimizes the space-time yield, based on the C-H-acidic compound of the formula (VI).

The reaction of the bis(hydroxymethyl) compounds of the formula (II) with the aldehyde or ketone (IV) and the orthoester (III) in accordance with the present method is promoted by acidic catalysts. Advantageously, therefore, a strong mineral acid, such as hydrochloric acid or sulfuric acid, or acid salts of the latter are used. Other suitable catalysts are acidic fixed-bed catalysts, e.g. ion exchangers on an organic basis, such as phenolformaldehyde resins which contain sulfonic acid groups, or on an inorganic basis, such as acidic montmorillonites. The acidic catalysts are generally used in amounts of from 0.05 to 5.0 percent by weight, preferably from 0.05 to 2.0 percent by weight, based on the reaction mixture. Acidic fixed-bed catalysts are expediently used in amounts of from 2 to 10 percent by weight. Their proportion is even higher if the starting material mixture is passed over fixed acidic ion exchangers.

Particularly suitable catalysts are alkali metal hydrogen sulfates, such as sodium hydrogen sulfate, on their own or together with sulfuric acid. Even if the reaction mixture is not neutralized, the isolation of the 1,3-dioxane compounds of the formula (I) by distillation gives rise to hardly any decomposition. But even if other acidic catalysts are used, the otherwise necessary—and under industrial conditions very laborious—aqueous work-up of the reaction mixture can be dispensed with, if the catalyst is neutralized, e.g. by filtration or neutralization with a base such as sodium hydroxide, sodium alcoholate, sodium carbonate or sodium hydrogen carbonate.

The 1,3-dioxane compounds of the formula (I) can be isolated by fractional distillation of the reaction mixture freed from low-boiling components, if they are not being subjected to further reaction in the reaction mixture. This latter procedure is advisable, in particular, with 1,3-dioxane compounds derived from long-chain aldehydes or ketones.

Having described the present invention, reference will now be made to certain examples which are provided solely for purposes of illustration and are not intended to be limitative.

EXAMPLE 1 (comparative example)

Diethyl 1,5-dioxaspiro[5.5]undecane-3,3-dicarboxylate

A stirred mixture of 165.0 g of diethyl bis(hydroxymethyl)malonate (98%, 0.75 mol), 75.3 g of cyclohexanone and 500 g of cyclohexane as a solvent and entrainer was admixed with 1.0 g of sulfuric acid. The mixture was then heated to reflux temperature (70–80° C.), the reaction water formed being continuously removed over a period of 5 hours.

After the reaction was complete, the reaction mixture was cooled to room temperature and introduced into dilute, excess aqueous sodium hydrogen carbonate solution. The aqueous phase was re-extracted with methyl t-butyl ether, and the combined organic phases were washed once with water. After drying over sodium sulfate the solvents were distilled off on a rotary evaporator, and the product was isolated by distillation in an oil pump vacuum. This gave 168.4 g of target product (75% of the theoretical yield, based on the diethyl bis(hydroxymethyl)malonate used) with a boiling point of 140° C./0.2 mm. The purity, determined by gas chromatography, was 97 to 98 FID percent by area.

EXAMPLE 2

Diethyl 1,5-dioxaspiro[5.5]undecane-3,3-dicarboxylate

A suspension, stirred at room temperature, of 60.0 g of paraformaldehyde (2.0 mol) and 0.25 g of sodium methylate in 40.0 g of ethanol had 160.2 g of diethyl malonate (1.0 mol) added to it gradually over a period of 1.75 hours, the internal temperature being kept, by cooling, between 20° C. and 30° C. The reaction was allowed to continue for 2 hours at 50° C., before 148.2 g of trimethyl orthoformate were added gradually. After the addition of 0.4 g of sulfuric acid, the mixture was heated to 50° C. for a further 2.5 hours, weak reflux being noticeable. At a bottom temperature of up to 80° C., 129.0 g of distillate having a boiling range from 30° C. to 55° C. were then taken off, followed by the gradual addition, over a period of 1.45 hours, of 98.0 g of cyclohexanone (1.0 mol), a further 25.9 g of low-boiling components having a boiling range of from 36° C. to 44° C. being distilled off.

After cooling to room temperature, the reaction mixture underwent aqueous work-up by being stirred into 600 ml of sodium hydrogen carbonate solution, the organic phase being separated off and the aqueous phase being extracted twice with portions of 200 ml of methyl t-butyl ether. Subsequent fractional distillation without using a column gave 197.8 g of colorless target product (63.3% of the theoretical yield, based on diethyl malonate used) with a purity, determined by gas chromatography, of 95 FID percent by area.

EXAMPLE 3

Diethyl 1,5-dioxaspiro[5.5]undecane-3,3-dicarboxylate

A suspension, stirred at room temperature, of 148.4 g of trimethyl orthoformate (1.4 mol) and 63.0 g of paraformaldehyde (2.1 mol) was admixed with 10.0 g of ethanol and 0.25 g of sodium ethanolate. The mixture was then heated to 50° C., and 160.2 g of diethyl malonate (1.0 mol) were added gradually over a period of 1.75 hours. At first, the reaction mixture thus obtained was stirred for a further 2 hours at 50° C., followed by cooling to room temperature. With stirring, 0.37 g of sulfuric acid and 1.0 g of sodium hydrogen sulfate were added, after which the temperature was initially, for a further 2 hours, regulated to 50° C. In the course of subsequent heating to 80° C., 72.3 g of low-boiling components were taken off, and 98.0 g of cyclohexanone (1.0 mol) were then gradually added over a period of 1.75 hours, a further 74.4 g of low-boiling components distilling over. Subsequent fractional distillation without using a column gave 246.2 g of colorless target product (78.3% of the theoretical yield, based on diethyl malonate used) with a purity, determined by gas chromatography, of 95.4 FID percent by area.

EXAMPLE 4

Diethyl 1,5-dioxaspiro[5.5]undecane-3,3-dicarboxylate

The same procedure was followed as in Example 3, except that the isolation of the product by distillation was preceded by an aqueous work-up employing saturated sodium hydrogen carbonate solution. Subsequent fractional distillation without using a column afforded 253.0 g of colorless target product (80% of the theoretical yield, based on diethyl malonate used) with a purity, determined by gas chromatography, of 96 FID percent by area.

EXAMPLE 5

Diethyl 1,5-dioxaspiro[5.5]undecane-3,3-dicarboxylate

A suspension, stirred at room temperature, of 60.0 g of paraformaldehyde (2.0 mol) and 0.25 g of sodium ethylate in 50.0 g of ethanol had 160.2 g of diethyl malonate (1.0 mol) added to it gradually over a period of one hour, the internal temperature being kept, by cooling, between 20° C. and 30° C. The reaction was allowed to continue for 2 hours at 50° C., before 0.4 g of sulfuric acid and 1.0 g of sodium hydrogen sulfate were added and 98 g of cyclohexanone (1.0 mol) were gradually added over a period of 5 minutes. The mixture was heated to 50° C. for one hour, 112.2 g of trimethyl orthoformate were added gradually over a period of one hour, after which the reaction was allowed to continue for a further 2 hours at 50° C. Subsequent heating caused 159.6 g of low-boiling components to distill over. The remaining residue was fractionated in an oil pump vacuum, 213.8 g of target product [lacuna] column gave 197.8 g of colorless target product (74.1% of the theoretical yield, based on diethyl malonate used). The purity, determined by gas chromatography, was 96 FID percent by area.

EXAMPLE 6

Diethyl 2-isopropyl-1,3-dioxane-5,5-dicarboxylate

A mixture of 165.0 g of diethyl bis(hydroxymethyl) malonate, 83.4 g of trimethylorthoformate and 0.6 g of sodium hydrogen sulfate was heated, with stirring, to 50° C. for 30 minutes and then to 60° C. for 90 minutes. Over a period of 45 minutes, 81.0 g of isobutyraldehyde were then added gradually, the internal temperature being kept to 60° C. by gentle cooling. The low-boiling components formed were distilled off up to a bottom temperature of 120° C., and 1.0 g of sodium carbonate was then added to neutralize the catalyst. Subsequent distillation in an oil pump vacuum afforded 168.2 g of colorless target product (82% of the theoretical yield, based on the diethyl bis(hydroxymethyl) malonate used) with a boiling point of 110° C./1 mm. The purity, determined by gas chromatography, was 98 FID percent by area.

EXAMPLE 7

Diethyl 2-isopropyl-1,3-dioxane-5,5-dicarboxylate

The same procedure was followed as in Example 6, except that no sodium carbonate was added before the product was isolated by distillation. The yield of colorless target product was 164.6 g (80% of the theoretical yield, based on diethyl bis(hydroxymethyl)malonate used). The product had a purity, determined by gas chromatography, of 98 FID percent by area.

EXAMPLE 8

Diethyl 2-isopropyl-1,3-dioxane-5,5-dicarboxylate

A suspension, stirred at room temperature, of 30.0 g of paraformaldehyde (1.0 mol) in 25.0 g of ethanol was admixed with 0.13 g of sodium ethanolate. The mixture was stirred for 20 minutes, and 80.1 g of diethyl malonate (0.5 mol) were then added gradually over a period of 1.5 hours, the internal temperature being kept between 26° C. and 28° C. At first, the reaction mixture thus obtained was stirred for a further 2 hours at 50° C., followed by cooling to room temperature. With stirring, 0.18 g of concentrated sulfuric acid, 55.7 g of trimethyl orthoformate (0.53 mol) and 1.5 g of sodium hydrogen sulfate monohydrate were added, after which the temperature was initially, for a further 3.0 hours, regulated to 50° C.

Then, over a period of 2 hours, 54.0 g of isobutyraldehyde (0.75 mol) were gradually added, a 20 cm packed column being used, with bottom temperatures of between 60° C. and 80° C., to take off a total of 81.3 g of low-boiling components having a boiling range from 23° C. to 68° C. After a further 19.1 g of low-boiling components were distilled off by the bottom temperature being raised to 120° C., the remaining residue was fractionated in an oil pump vacuum without a column being used. This gave 97.6 g of colorless target product (69.8% of the theoretical yield, based on diethyl malonate used) having a purity, determined by gas chromatography, of 98 FID percent by area.

EXAMPLE 9

Ethyl 3-cyano-1,5-dioxaspiro[5.5]undecane-3-carboxylate

A mixture, stirred at from 0° C. to 10° C., of 62.0 g of paraformaldehyde (2.1 mol), 200 g of ethanol and 0.25 g of sodium ethanolate had 113.0 g of ethyl cyanoacetate (1.0 mol) gradually added to it over a period of 2.0 hours. The reaction mixture was then stirred for a further 1 hour at 10° C. before being warmed to room temperature over a period of 10 minutes. The solution thus obtained was freed from solvent on a rotary evaporator at a vacuum of 8 mbar, affording 175.1 g of a colorless, highly viscous oil.

This was dissolved in 157.1 g (1.48 mol) of trimethyl orthoformate, before 0.36 g of concentrated sulfuric acid was added with stirring and the mixture was heated to 50° C. for 2 hours. Then 98.0 g of cyclohexanone (1.0 mol) were added dropwise over a period of 1 hour. The reaction was allowed to continue for a further 1.5 hours at 50° C., and the low-boiling components formed were initially distilled off in a water pump vacuum at a bottom temperature of at most 60° C., and were then distilled off completely at 2.5 mbar.

There remained 221.3 g of a pale-yellow, highly viscous oil which, according to NMR analysis (80 MHZ), contained about 30% of target product.

EXAMPLE 10

Ethyl 2-isopropyl-5-cyano-1,3-dioxane-5-carboxylate

A mixture, stirred at from 0° C. to 10° C., of 62.0 g of paraformaldehyde (2.1 mol), 200 g of ethanol and 0.25 g of sodium ethanolate had 113.0 g of ethyl cyanoacetate (1.0 mol) gradually added to 2.0 hours. The reaction mixture was then stirred for a further 1 hour at 10° C. before being warmed to room temperature over a period of 10 minutes. The solution thus obtained was freed from solvent on a rotary evaporator at a vacuum of 8 mbar, affording 175.1 g of a colorless, highly viscous oil.

This was dissolved in 157.1 g (1.48 mol) of trimethyl orthoformate, before 0.36 g of concentrated sulfuric acid was added with stirring and the mixture was heated to 50° C. for 2 hours. Then 123.5 g of isobutyraldehyde (1.7 mol) were added dropwise over a period of 0.75 hours. The reaction was allowed to continue for a further 0.5 hours at 50° C., and the low-boiling components formed were initially distilled off in a water pump vacuum at a bottom temperature of at most 60° C., and were then distilled off completely at 2.5 mbar.

There remained 239.1 g of a pale-yellow, highly viscous oil which, according to NMR analysis (80 MHZ), contained about 30% of target product.

Having further described the present invention, it will now be apparent to one of ordinary skill in the art that many changes and modifications may be made to the embodiments described above without departing from the spirit and the scope of the present invention.

What is claimed as new and is desired to be secured by Letters Patent of the United States is:

1. A method for preparing 1,3-dioxane compounds of the formula (I):

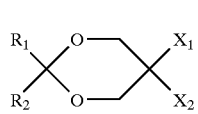

(I)

wherein $R^1$ and $R^2$, independently of one another, each represents hydrogen or a hydrocarbon radical; and $X^1$ and $X^2$ independently of one another, each represents an electronegative group, which method comprises reacting a bis (hydroxymethyl) compound of the formula (II):

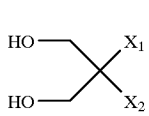

(II)

wherein $X^1$ and $X^2$ each, independently of one another, are as defined above, with an orthocarboxylic acid ester of the formula (III):

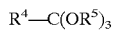

in which $R^4$ represents hydrogen or a hydrocarbon radical, $R^5$ represents a hydrocarbon radical to form a cyclic orthocarboxylic acid ester, and with an aldehyde or ketone with the formula (IV):

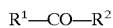

wherein $R^1$ and $R^2$ each, independently of one another, are as defined above.

2. The method of claim 1, wherein $R^1$ and $R^2$ each, independently of one another, represent hydrogen, alkyl, aralkyl, aryl or cycloalkyl, each having up to 12 carbon atoms; or $R^1$ and $R^2$ together form an alkylene radical having from 4 to 11 carbon atoms; and $X^1$ and $X^2$ each, independently of one another, represent COOR, $CONR_2$, CN, $NO_2$, C(OR)=$NR_2$ or COR, R representing hydrogen, alkyl, aralkyl, aryl or cycloalkyl, each having up to 12 carbon atoms; with the proviso that (i) the substituents $X^1$ and $X^2$ cannot both simultaneously represent COOH, and (ii) if the two substituents $X^1$ and $X^2$ simultaneously represent COR, and if wherein the two substituents R may also represent an alkylene radical having from 2 to 9 carbon atoms.

3. The method of claim 1, wherein $X^1$ and $X^2$ each independently represent CN or COOR'; and R' is a $C_{1-4}$-alkyl radical.

4. The method of claim 1, wherein the bis (hydroxymethyl) compound of the formula (II) is successively reacted with the orthocarboxylic acid ester of the formula (III) and the aldehyde or ketone of the formula (IV).

5. The method of claim 1, wherein the reaction of the bis(hydroxymethyl) compound of the formula (II) with the aldehyde or ketone of the formula (IV) is carried out in the presence of an acidic catalyst.

6. The method of claim 5, wherein the acidic catalyst is an alkali metal hydrogen sulfate, optionally together with sulfuric acid, or an acidic fixed-bed catalyst.

7. The method of claim 1, wherein the reaction is carried out batchwise at from about 0 to 80° C. or continuously at a temperature up to 200° C., the reaction time being selected in accordance with the reaction temperature so that virtually no decomposition takes place.

8. The method of claim 7, wherein said reaction is carried out batchwise at a temperature of from about 20° to 50° C.

9. The method of claim 7, wherein the reaction is carried out batchwise and the temperature is raised toward the end of the reaction.

10. The method of claim 1, wherein low-boiling components are distilled off during the reaction from the reaction mixture.

11. The method of claim 1, wherein the 1,3-dioxane compounds I are isolated by fractional distillation of the reaction mixture freed from low-boiling components.

12. The method of claim 1, wherein the bis (hydroxymethyl) compound of the formula (II) is prepared by reacting a C-H-acidic compound of the formula (VI):

in which $X^1$ and $X^2$ are as defined above, with formaldehyde or a formaldehyde-releasing compound, and without isolation being is reacted in the reaction mixture.

13. The method of claim 12, wherein the reaction is carried out in an orthocarboxylic acid ester as the solvent.

14. The method of claim 1, wherein said bis (hydroxymethyl) compound of the formula (II) is selected from the group consisting of dimethyl bis(hydroxymethyl) malonate, diethyl bis(hydroxymethyl) malonate, di-n-propyl bis(hydroxymethyl) malonate, diisobatyl bis (hydroxymethyl) malonate, dibenzyl bis(hydroxymethyl) malonate, di-2-ethylhexyl bis(hydroxymethyl) malonate, ethyl bis(hydroxymethyl)-N,N-dimethyl(carbamideacetate, bis(hydroxymethyl)-N,N,N',N'-tetramethylmalonamide, bis (hydroxymethyl) malonitrile, ethyl bis(hydroxymethyl) cyanoacetate, n-butyl bis-(hydroxymethyl) cyanoacetate, ethyl bis(hydroxymethyl) nitroacetate, 3,3-bis (hydroxymethyl) acetylacetane and 2,2-bis(hydroxymethyl) cyclododeca-1,3-dione.

15. The method of claim 1, wherein said orthocarboxylic acid ester of the formula (III) is selected from the group consisting of diethyl orthoformate, triisobutyl orthoformate and trimethylorthoformate.

16. The method of claim 1, wherein said aldehyde of the formula (IV) is selected from the group consisting of formaldehyde, acetaldehyde, n-butyraldehyde, isobutyraldehyde, benzaldehyde, and phenylacetaldehyde.

17. The method of claim 1, wherein said ketone of the formula (IV) is selected from the group consisting of acetone, methyl ethyl ketone, diisopropyl ketone, cyclohexanone and cyclododecanone.

18. The method of claim 1, wherein said aldehyde or ketone of the formula (IV) is employed in an amount of from a stoichiometric amount to up to a stoichiometric excess of up to 200%.

* * * * *